United States Patent
Holweger et al.

(10) Patent No.: US 11,091,845 B2
(45) Date of Patent: Aug. 17, 2021

(54) METHOD FOR STORING ENERGY IN THE FORM OF HYDRAZINE CARBONATE

(71) Applicant: Schaeffler Technologies AG & Co. KG, Herzogenaurach (DE)

(72) Inventors: Walter Holweger, Epfendorf (DE); Moritz Wegener, Erlangen (DE); Yashar Musayev, Nuremberg (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 188 days.

(21) Appl. No.: 16/343,047

(22) PCT Filed: Sep. 22, 2017

(86) PCT No.: PCT/DE2017/100808
§ 371 (c)(1),
(2) Date: Apr. 18, 2019

(87) PCT Pub. No.: WO2018/095458
PCT Pub. Date: May 31, 2018

(65) Prior Publication Data
US 2020/0087800 A1    Mar. 19, 2020

(30) Foreign Application Priority Data
Nov. 22, 2016    (DE) .................. 102016223001.8

(51) Int. Cl.
*C25B 1/04*    (2021.01)
*C01B 21/16*    (2006.01)
*C25B 1/26*    (2006.01)

(52) U.S. Cl.
CPC .............. *C25B 1/04* (2013.01); *C01B 21/16* (2013.01); *C25B 1/26* (2013.01)

(58) Field of Classification Search
CPC .. C25B 1/04; C25B 1/26; C25B 15/08; C01B 21/16; Y02E 60/50; Y02E 60/36;
(Continued)

(56) References Cited

U.S. PATENT DOCUMENTS 3,077,383 A    2/1963    Mundil
3,251,755 A *  5/1966    Mayland ................. C01B 21/16
                                                  205/551
4,248,690 A    2/1981    Conkling

FOREIGN PATENT DOCUMENTS

AT    514461 A1      1/2015
AT    516196 A1 *   3/2016  ............. C25B 15/08
(Continued)

OTHER PUBLICATIONS

Author: Konrad Meier Title: Hydrogen Production with Sea Water Electrolysis Using Norwegian Offshore Wind Energy Potentials, Published online by Springerlink.com Date: May 13, 2014 Country: Norway.

*Primary Examiner* — Anthony J Zimmer

(57) ABSTRACT

Energy storage is accomplished by producing hydrazine carbonate and later reconverting the hydrazine carbonate to release the energy. Sea water is firstly used in an electrolysis process to prepare hypochlorite. The hypochlorite reacts as a result of introduction of ammonia to produce monochloramine and then hydrazine. The hydrazine reacts as a result of introduction of carbon dioxide to give hydrazine carbonate. To release the energy, the hydrazine carbonate liberates hydrogen or at least a hydrogen-containing gas by reaction over a noble metal-free catalyst. The hydrogen may then be enriched before being fed to a fuel cell.

13 Claims, 1 Drawing Sheet

(58) Field of Classification Search
CPC ..... Y02P 70/50; Y02P 20/133; H01M 8/0606; C07C 281/00
See application file for complete search history.

(56) References Cited

FOREIGN PATENT DOCUMENTS

| | | | |
|---|---|---|---|
| AT | 516196 A1 | 3/2016 | |
| DE | 3030324 A1 | 7/1981 | |
| GB | 754826 A * | 8/1956 | ............ C01B 21/16 |

* cited by examiner

METHOD FOR STORING ENERGY IN THE FORM OF HYDRAZINE CARBONATE

CROSS-REFERENCE TO RELATED APPLICATIONS

This application is the U.S. National Phase of PCT Appln. No. PCT/DE2017/100808 filed Sep. 22, 2017, which claims priority to DE 10 2016 223 001.8 filed Nov. 22, 2016, the entire disclosures of which are incorporated by reference herein.

TECHNICAL FIELD

The disclosure relates to a process for storing energy in the form of hydrazine carbonate and subsequently reconverting the hydrazine carbonate into usable energy.

BACKGROUND

AT 514 461 A1 discloses a process for storing energy in the form of hydrazine carbonate and subsequently reconverting the hydrazine carbonate into usable energy. Water is converted in an electrolysis process into hydrazine carbonate by means of energy and with introduction of nitrogen and carbon dioxide in the presence of a transition metal catalyst which decreases the activation energy of the stable nitrogen-nitrogen triple bond. The anode is here surrounded by an oxygen-impermeable diaphragm. A metal salt is used to inhibit hydrogenolytic cleavage of the hydrazine. The hydrazine carbonate is isolated in the form of a solid or in the form of a concentrated solution from the mixture, and the hydrazine carbonate is later decomposed thermally in order to recover the energy by combustion of the hydrogen or by use of the hydrogen in a fuel cell.

SUMMARY

It is an object of the present disclosure to propose an inexpensive and industrially usable process for the long-term storage of energy in the form of hydrazine carbonate and also the subsequent reconversion of the hydrazine carbonate into usable energy. In particular, it is an object of the present disclosure to provide sustainable energy storage proceeding from readily available raw materials.

DETAILED DESCRIPTION

Figure 1:
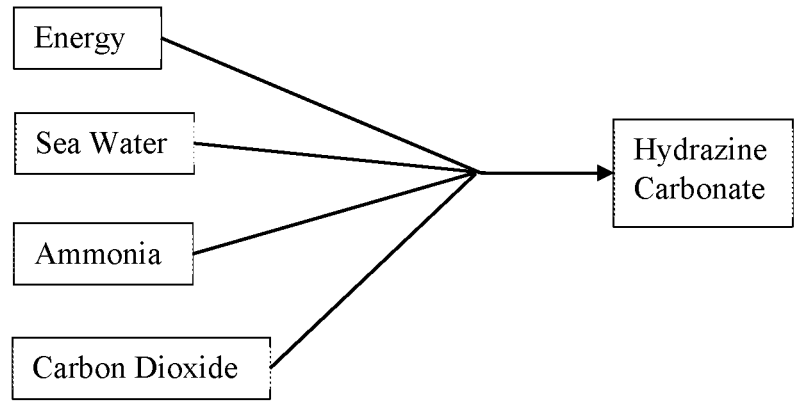
FIG. 1 illustrates a process for storing energy as Hydrazine Carbonate.
Figure 2:
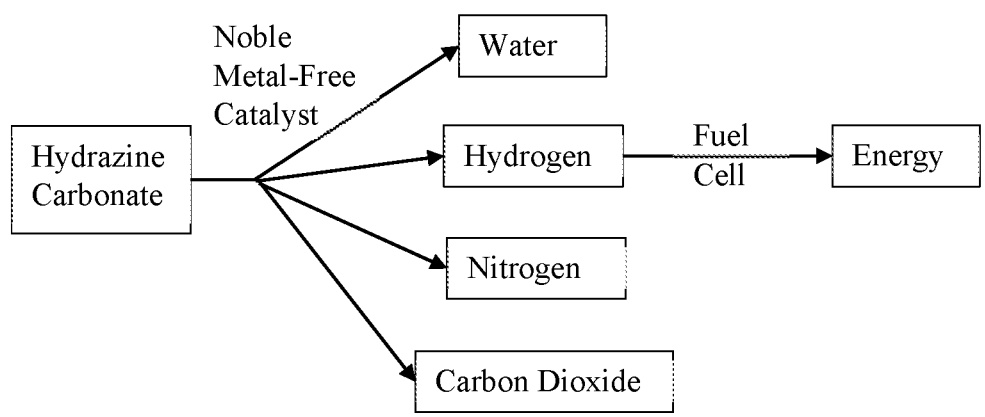
FIG. 2 illustrates a process for releasing energy stored as Hydrazine Carbonate.

In the process for storing energy in the form of hydrazine carbonate and subsequently reconverting the hydrazine carbonate into usable energy, sea water is firstly used in an electrolysis process to prepare hypochlorite, where the hypochlorite reacts as a result of introduction of ammonia via the formation of monochloramine to give hydrazine and where the hydrazine subsequently reacts as a result of introduction of carbon dioxide to give hydrazine carbonate, where the hydrazine carbonate liberates hydrogen or at least a hydrogen-containing gas by reaction over a noble metal-free catalyst in order to liberate the stored energy and where the hydrogen or the at least hydrogen-containing gas is intended for being fed to a fuel cell or burnt in order to release the usable energy. In particular, the hydrogen-containing gas is a gas mixture of at least hydrogen and nitrogen.

Both hydrazine and hydrazine carbonate are known at least from the abovementioned AT 514 461 A1. Accordingly, hydrazine has an aqueous form and is mainly used industrially as a reducing agent and as a free-radical scavenger. Hydrazine carbonate is a nonvolatile, water-soluble salt which is used as an antioxidant in the chemical industry.

The sea water ($H_2O$) is used to prepare hypochlorite ($OCl^-$) by sea water electrolysis. The following reactions take place here:

$$2H_2O + 2e^- \rightarrow H_2 + 2OH^-$$ Cathode reaction:

$$2Cl^- - 2e^- \rightarrow Cl_2,$$ Anode reaction:

$$Cl_2 + 2OH^- \rightarrow H_2O + OCl^- + Cl^-$$ Reaction 1:

The energy used in the sea water electrolysis for preparing hypochlorite is preferably obtained from renewable energy sources. In particular, this energy is made up of wind power energy, solar energy and/or bioenergy.

The hypochlorite reacts as a result of introduction of ammonia ($NH_3$) via the formation of monochloramine ($NH_2Cl$) to give hydrazine ($N_2H_4$). In other words, gaseous ammonia is firstly introduced into the hypochlorite-comprising aqueous solution, resulting in water and monochloramine being formed according to reaction 2.

$$NH_3 + HOCl \rightarrow NH_2Cl + H_2O$$ Reaction 2:

According to a subsequent reaction 3, the monochloramine reacts with the ammonia and forms hydrogen chloride (HCl) and hydrazine.

$$NH_2Cl + NH_3 \rightarrow N_2H_4 + HCl$$ Reaction 3:

The hydrazine then reacts according to reaction 4 as a result of introduction of carbon dioxide ($CO_2$) to give hydrazine carbonate ($(N_2H_5)_2CO_3$).

$$N_2H_4 + CO_2 \rightarrow (N_2H_5)_2CO_3$$ Reaction 4:

The carbon dioxide is preferably taken from an exhaust gas stream of a combustion plant. For example, the exhaust stream is produced by a coal-fired power station. Exploitation of the high concentration of carbon dioxide in the exhaust gas stream of the combustion plant is particularly advantageous.

The hydrazine carbonate serves as stable, long-term store for hydrogen ($H_2$). To liberate the energy stored in the hydrazine carbonate, a noble metal-free catalyst is used, with the hydrogen or at least the hydrogen-containing gas being liberated according to reaction 5.

As noble metal-free catalyst, preference is given to using a catalyst composed of oxidic materials, for example of $Al_2O_3$, Cu-doped $Al_2O_3$ or a calcium-aluminum silicate such as $CaAl_2Si_3O_8(OH)_4 \cdot H_2O$. Over such a noble metal-free catalyst, for example $CaAl_2Si_3O_8(OH)_4 \cdot H_2O$, the hydrazine carbonate is decomposed, in particular at temperatures in the range from 100 to 150° C., into hydrogen, $CO_2$ and water. In particular, the catalyst has a high porosity. The porosity serves, in particular, to increase the reactive surface area of the catalyst.

$$(N_2H_5)_2CO_3 \rightarrow N_2 + H_2 + CO_2 + H_2O$$ Reaction 5:

A separation step for enriching the hydrogen is preferably provided after the reaction of the hydrazine carbonate over the noble metal-free catalyst. In particular, the separation step is provided for separating the hydrogen from the nitrogen. The carbon dioxide liberated according to reaction 5 is the carbon dioxide which was previously introduced and reversibly bound in the hydrazine carbonate. The process is thus $CO_2$-neutral.

In order to liberate the stored energy, in particular to liberate the hydrogen or to liberate the at least hydrogen-containing gas by reaction over the noble metal-free catalyst, the hydrazine carbonate is heated to less than 100° C. The hydrogen or at least the hydrogen-containing gas is preferably fed to a fuel cell or burnt in order to release the usable energy. For example, the hydrogen or at least the hydrogen-containing gas is fed to a low-temperature fuel cell.

The use of the hydrogen in fuel cells counters, in particular, the discontinuity of the supply of power from renewable energy sources. Furthermore, the hydrogen stored in the hydrazine carbonate can be used both for fuel cells in stationary applications and also for fuel cells in mobile applications such as passenger cars, goods vehicles, ships and aircraft.

The invention claimed is:

1. A process for storing energy in the form of hydrazine carbonate and subsequently reconverting the hydrazine carbonate into usable energy,
wherein an electrolysis process uses sea water to prepare hypochlorite, wherein the hypochlorite reacts as a result of introduction of ammonia via the formation of monochloramine to give hydrazine and wherein the hydrazine subsequently reacts as a result of introduction of carbon dioxide to give hydrazine carbonate, and wherein the hydrazine carbonate liberates $H_2$ or at least a gas containing $H_2$ by reaction in the presence of a noble metal-free catalyst.

2. The process of claim 1,
wherein a separation step for enriching $H_2$ is provided after the reaction of the hydrazine carbonate in the presence of the noble metal-free catalyst.

3. The process of claim 1,
wherein the $H_2$ or gas containing $H_2$ is fed to a fuel cell.

4. The process of claim 1,
wherein the carbon dioxide is taken from an exhaust gas stream of a combustion plant.

5. The process of claim 1,
wherein a catalyst composed of oxidic materials is used as the noble metal-free catalyst.

6. The process of claim 1,
wherein the energy used in the sea water electrolysis for preparing hypochlorite is obtained from renewable energy sources.

7. The process of claim 1,
wherein the hydrazine carbonate is heated to less than 100° C. by reaction in the presence the noble metal-free catalyst.

8. A process for storing and releasing energy comprising:
storing energy by conducting an electrolysis process to prepare hypochlorite from sea water;
introducing ammonia which reacts with the hypochlorite to form hydrazine;
introducing carbon dioxide which react with the hydrazine to give hydrazine carbonate; and
reacting the hydrazine carbonate in the presence of a noble metal-free catalyst to liberate $H_2$ or gas containing $H_2$.

9. The process of claim 8, further comprising enriching the hydrogen after the reaction of the hydrazine carbonate in presence of the noble metal-free catalyst.

10. The process of claim 8, further comprising feeding the $H_2$ or gas containing $H_2$ to a fuel cell.

11. The process of claim 8, wherein the carbon dioxide is taken from an exhaust gas stream of a combustion plant.

12. The process of claim 8, wherein the noble metal-free catalyst comprises oxidic materials.

13. The process of claim 8, wherein the hydrazine carbonate is heated to less than 100° C. by reaction in the presence of the noble metal-free catalyst.

* * * * *